United States Patent
Kung

[19]

[11] Patent Number: 6,117,130
[45] Date of Patent: Sep. 12, 2000

[54] CORING DEVICE FOR MYOCARDIAL REVASCULARIZATION

[75] Inventor: Robert T. V. Kung, Andover, Mass.

[73] Assignee: Abiomed, Inc., Danvers, Mass.

[21] Appl. No.: 09/160,375

[22] Filed: Sep. 24, 1998

[51] Int. Cl.[7] .................................................. A61B 18/04
[52] U.S. Cl. .................................................. 606/28; 606/41
[58] Field of Search ................... 606/27–31, 37, 606/39, 32, 41; 604/114; 128/898

[56] References Cited

U.S. PATENT DOCUMENTS

| | | | |
|---|---|---|---|
| 4,682,596 | 7/1987 | Bales et al. | 606/39 |
| 4,748,979 | 6/1988 | Hershenson | 606/28 |
| 4,838,280 | 6/1989 | Haaga | 600/564 |
| 5,611,798 | 3/1997 | Eggers | 606/31 |
| 5,766,164 | 6/1998 | Mueller et al. | 606/15 |
| 5,807,392 | 9/1998 | Eggers | 606/31 |
| 5,911,719 | 6/1999 | Eggers | 606/31 |
| 5,911,729 | 6/1999 | Shikhman et al. | 606/181 |
| 5,944,716 | 8/1999 | Hektner | 606/45 |
| 6,042,590 | 3/2000 | Sporri et al. | 606/135 |

*Primary Examiner*—Michael Peffley
*Attorney, Agent, or Firm*—Samuels, Gauthier & Stevens, LLP

[57] ABSTRACT

Devices are disclosed for performing transmyocardial revascularization (TMR), percutaneous revascularization and other thermal tissue therapies. The invention utilizes a coring needle with an associated heating element to core out tissue to form a channel in the myocardium, and concurrently thermalize a thin tissue layer at the wall of the channel. The invention yields myocardial channels similar to those obtained with conventional techniques, but with lower energy requirements. The invention further new closure mechanisms for transmyocardial applications.

26 Claims, 4 Drawing Sheets

CORING DEVICE FOR MYOCARDIAL REVASCULARIZATION

BACKGROUND OF THE INVENTION

This invention relates generally to methods and devices for coring a channel in living tissue and more particularly to a heated, hollow boring device for coring a channel in the myocardium of the heart such that the wall of the channel is controllably thermalized.

Revascularization involves the restoration of the blood circulation of an organ or area, achieved by unblocking obstructed or disruptive blood vessels or by surgically implanting replacements. Transmyocardial revascularization (TMR) is a medical procedure for treating ischemic heart disease that involves coring holes in the myocardium of the heart to form a channel between the ventricle and the myocardium to revascularize the heart. Ischemic heart disease is a condition in which the heart muscle or myocardium does not receive an adequate nutritive blood supply. Transmyocardial Revascularization is used to supplement the blood supply to the heart by providing the ischemic inner surface (endocardium) direct access to blood within the ventricular chamber. Normally the endocardium does not have direct access to blood within the ventricular chamber and receives its nutritive blood supply entirely from the coronary arteries branching through the heart wall from its outer surface (epicardium).

Conventional approaches for performing TMR include laser techniques for coring myocardial tissue. A laser suitable to perform the technique and a method for revascularizing the heart is described in U.S. Pat. No. 4,658,817 and assigned to Children's Hospital Medical Center of Cincinnati, Ohio. Access to the myocardium is attained either through the epicardium or the endocardium, and using a laser, channels are cored into the myocardium to facilitate direct ventricular perfusion of the myocardium.

The laser technique cores the channel by evaporating tissue starting from the epicardium and ending at the endocardium. Bleeding is controlled by "finger" pressure, until clotting is attained and the surface puncture is closed.

In an alternative approach, a channel is created by evaporating tissue with a laser starting from the endocardium through the myocardium into the epicardium. An optical fiber for transmitting the laser light is injected by use of a catheter. The tissue drilling process must be terminated without epicardial burn-through to prevent copious loss of blood, and thus a sensor at the tip of the catheter is required to measure tissue thickness.

Laser TMR generally requires an energy of 30 to 60 Joules per pulse to generate a channel with a 1 mm diameter and a length of 2 cm, which is the typical thickness of the myocardium. Using d to represent the diameter of the channel and the length of the channel, the energy required to core the channel is derived using the heat of vaporization, $H_v$, for water which is assumed to comprise 80% of the tissue.

$$E_l = \frac{\pi}{4} d^2 l H_v$$

With a value of 2400 J/gm for the heat of vaporization for water, $H_v$, the laser energy required to core the tissue ($E_l$) is calculated to be 37.7 Joules. The actual energy required, found by experimental means, is approximately 20% higher due to the higher heat of vaporization of tissue, and the heat loss to surrounding tissue during the ablation process. The heat of vaporization of tissue is typically higher than water by a factor of two.

Furthermore, in order to avoid interference with the refractory period which is the short period during which the myocardium should not be unnecessarily stimulated, the TMR procedure must be synchronized with the heart action. A narrow pulse of approximately 40 ms is necessary to minimize interference with the heart's electrical activity.

It is well known that simple coring of the myocardium does not result in open channels in the tissue suitable for promoting revascularization, but if the wall of the channel is thermalized during the coring, the revascularization has been found to be more effective. The boundary thickness of the thermally denatured zone in the channel wall must be precisely controlled since thermal zones that are too thick result in excessive damage to the tissue of the myocardium. It has been found that a thermal zone of less than 0.1 mm is suitable for effective channel formation.

It is desirable to provide a method and a device to perform transmyocardial revascularization that does not require the expense and high energy requirements of a laser, while at the same time providing satisfactory coring for revascularization.

It is also desirable to provide a device to create channels within the myocardium for revascularization of the heart where the walls of the channels are thinly thermalized with a thermal zone of less than 0.1 mm.

It is an object of the invention to provide a method and device to perform transmyocardial revascularization that obviates the disadvantages of the prior art.

It is a further object of the invention to provide a method and device for performing transmyocardial revascularization that cores a channel into the myocardium, and thermalizes the wall of the channel during the process.

It is a still further object of the invention to provide a device for performing transmyocardial revascularization that operates at a lower energy level than that required using conventional laser techniques.

It is yet a further object of the invention to provide a device for performing transmyocardial revascularization that includes a sheath having hooks to promote rapid hemostasis after extraction of the device from the myocardium, when the coring is performed from the epicardial surface.

It is an additional object of the invention to provide a device for performing transmyocardial revascularization that allows for coring the tissue from the endocardium with a thermal needle which is attached to a catheter for percutaneous introduction.

SUMMARY OF THE INVENTION

The invention provides a needle for coring a channel into the myocardium to promote myocardial revascularization. In one aspect, a surgical device for coring tissue is provided that comprises a thermally and electrically insulated needle having a resistive coating layer on its outer wall. A conductive material coats a portion of the inner wall of the needle to provide an electrical return for the resistive coating layer. The resistive coating layer along with the conductive portion of the inner wall of the needle forms a resistive circuit. The resistive coating layer and the conductive portion are each connected to an electric terminal for connecting a voltage supply to energize the resistive circuit. In use, the needle heats the surrounding tissue to a temperature of at least 70° C. and more preferably to a temperature above 90° C. to at least partially denature a thin layer of tissue at the wall of the channel formed by the coring needle. The needle is further coated with a thin layer of electrically insulated material. A wedge like or beveled tip is coupled to the needle at its distal circumference to facilitate coring into the myocardial tissue.

In particular, it has been discovered that there are advantages in the use of a hollow thermal needle insofar as the needle can remove a "core" from the heart muscle and, following thermal treatment, this bore hole can remain patent to promote blood diffusion into ischemic heart tissue. By heating the walls of the bore holes created by the present invention, the inner surface of these channels is modified to reduce the likelihood of reclosure everywhere except at the outer surface of the heart. A closure sheath can then be deployed to ensure that blood from within the ventricles does not flow all the way through the heart and "leak" into the chest cavity.

In a further aspect, the needle is enclosed in a slidably mounted sheath having hooks for achieving hemostasis. As the needle is extracted from the tissue after coring the channel, the sheath remains in the channel opening. Upon later extraction of the sheath, the hooks clasp the folds of the tissue, and allow clips or clamps to be applied to achieve hemostasis.

BRIEF DESCRIPTION OF THE DRAWINGS

In FIG. 2A, a coring needle is shown at the end of a channel-forming procedure with the sheath disposed about the needle but not yet in contact with the tissue; FIG. 2B illustrates the insertion of the sheath into the channel; In FIG. 2C, the needle is removed and in FIG. 2D, the sheath is clamped to seal the channel;

In FIG. 5A the needle is disposed within the ventricle and adjacent to the heart wall; in FIG. 5B the needle penetrates the heart wall. In FIG. 5C heat is applied to the channel; and in FIG. 5D the needle is removed and a segment of the heart muscle extracted to create the new channel.

DETAILED DESCRIPTION

Figure 1:
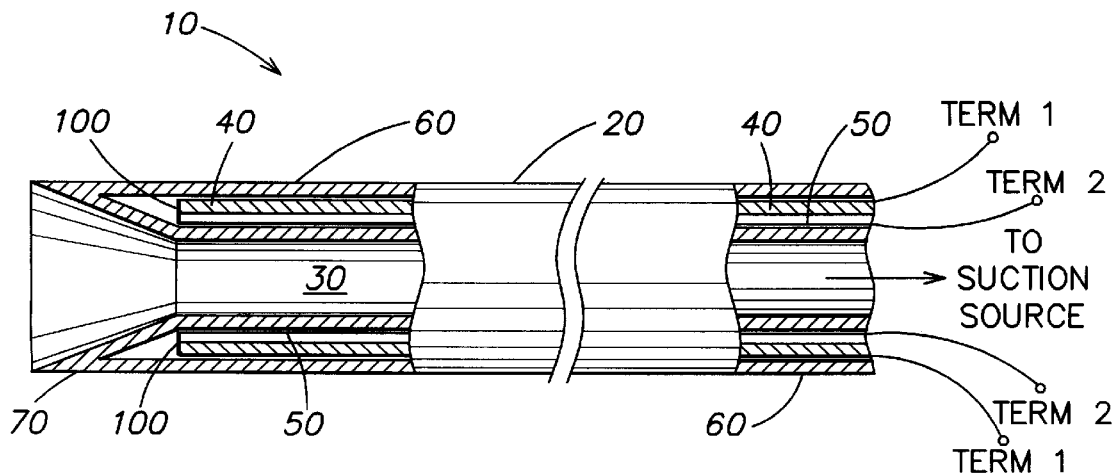
FIG. 1 is a partially cutaway, cross-sectional side view of a boring needle in accordance with the invention.

FIG. 1 shows a cutaway projected view of the body of a surgical needle 10 suitable for performing Transmyocardial Revascularization (TMR) in accordance with the invention. The needle 10 is used advantageously to core channels in the myocardium to promote revascularization of the heart by direct perfusion of blood from the ventricle. The needle 10 is used in conjunction with a catheter to gain access to the myocardium through either the epicardium or the endocardium. The needle 10 includes a thermally and electrically insulated, hollow shaft 20 with a bore 30 as shown. The needle is preferably cylindrical in shape with a preferred outside diameter of approximately 0.1 cm.

The needle 10 further includes a heating element (e.g., an electrical resistor) to deliver heat to the surrounding tissue once the needle has penetrated the heart muscle. In the illustrated embodiment, shaft 20 has a resistive coating layer 40 towards its outer wall which is preferably at least partially circumferentially located about the shaft. The shaft 20 can be constructed from a polymer, such as a polyimide or fluorocarbon polymer, and the resistive coating can be nichrome or graphite. However, one of ordinary skill in the art will recognize that other materials can provide equivalent functions. A conductive material 50 coats at least a portion of the inner wall of the hollow needle to provide an electrical return for the resistive coating layer. The conductive material 50 need not be circumferentially located around the shaft 20.

The inner wall of the needle can be constructed from, or coated with, a material which presents a polished or otherwise low friction surface. Such materials include, for example, metallic or fluorocarbon polymeric coatings. The resistive coating layer 40 along with the conductive portion of the inner wall of the needle 50 form a resistive, electrical circuit, which when energized is capable of generating sufficient heat to thermalize the wall of the channel that is cored. The heating results due to the electrical current passed through the resistive material, and causes the denaturation of a thin boundary layer of tissue in the process of channel creation.

The resistive layer 40 of the needle and the conductive portion 50 are each connected to a separate electrical terminal (TERM1, TERM2) in order to connect a voltage supply to the resistive circuit. The hollow needle is further coated with a thin layer of electrically insulated material 60 to prevent an electrical path through the myocardium. A wedge like or beveled tip 70 is optionally coupled to the needle at its distal end to facilitate coring into the myocardial tissue. The tip is sharpened so that a clean channel can be bored with minimal stress to surrounding tissue and is preferably fabricated from surgical stainless steel. The needle or a portion thereof can be constructed as a disposable which is maintained in a sterilized container until connected by the surgeon to the workstation.

Figure 1A:
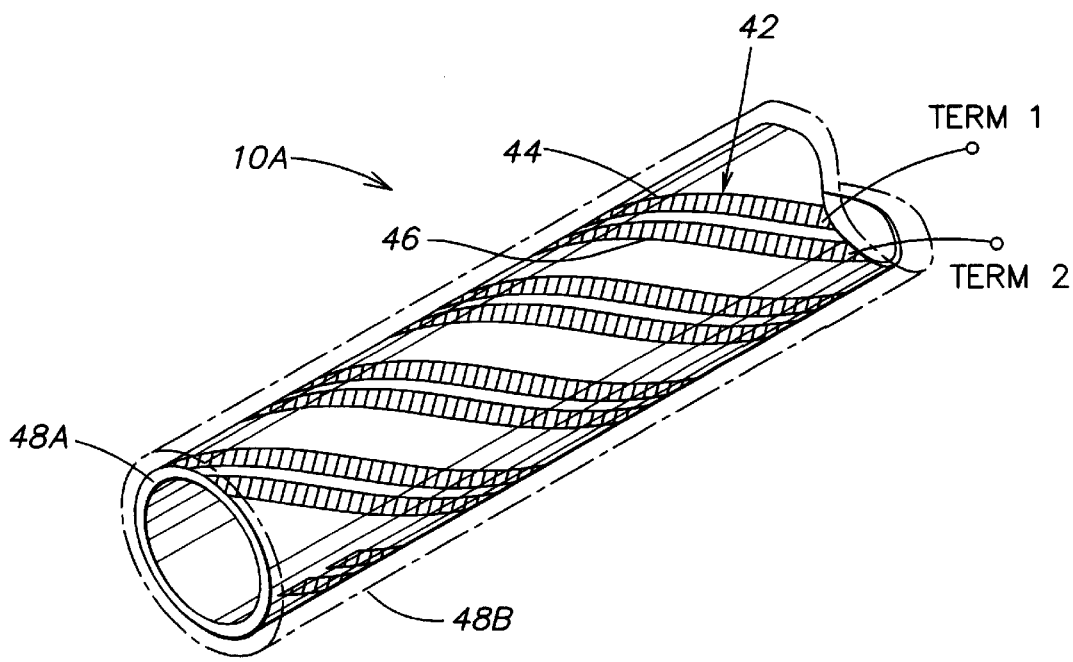
FIG. 1A is a partial cutaway side view of a boring needle in accordance with an alternative embodiment of the invention.

FIG. 1A illustrates another embodiment of a needle 10A according to the invention with an alternative heating element 42 which can be wrapped about a boring needle structure. The resistive circuit in this embodiment comprises a double helical winding of strip resistors 44 and 46. The heating element 42 can be contained between two layers 48A and 48B of a laminate material, such as polyimides or polyesters, that will have thermal properties such that they will not melt or otherwise degrade at the temperature of heating element operation. (Outer layer 48B is shown in phantom in FIG. 1A.)

Figure 2:
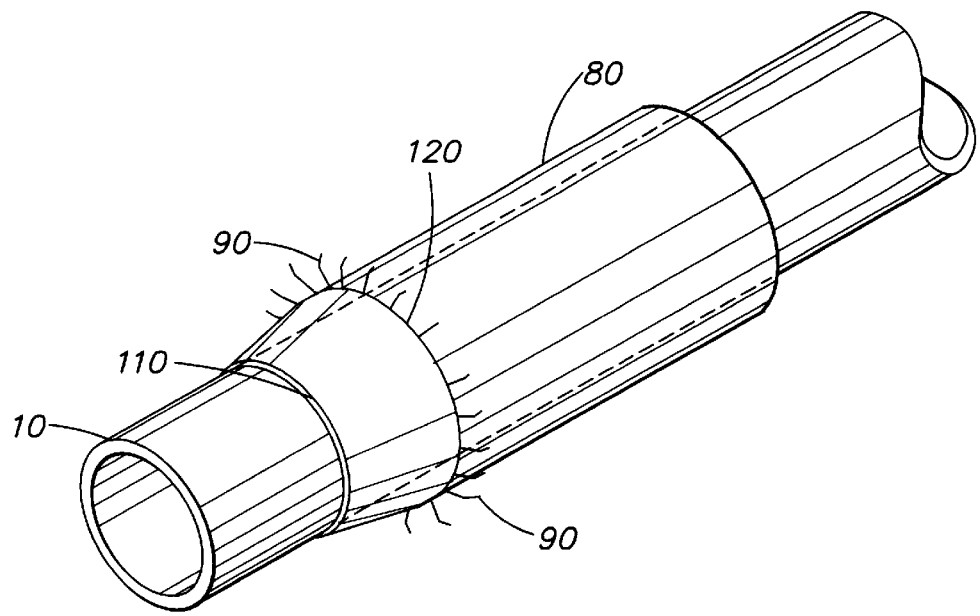
FIG. 2 is a perspective view of the boring needle of FIG. 1 with a surrounding concentric sheath having structural elements which can assist in post-operative hemostasis in accordance with the invention.

As is shown in FIG. 2, needle 10 is optionally enclosed in a slidably mounted sheath 80 having hooks 90 for achieving hemostasis. As the needle is extracted from the tissue after coring the channel, the tip of the sheath remains in the channel. Upon subsequent extraction of the sheath, hooks 90 clasp the folds of the punctured tissue, and allow clips or clamps to be easily applied to achieve hemostasis.

The needle sheath 80 is thin walled and of sufficient diameter to allow the needle to pass easily through it. The leading edge has a tapered wall thickness to avoid damage to surrounding tissue. The sheath can be composed of a thermally insulating material and preferably is of sufficient flexibility to facilitate closure. At its distal end, the outer surface of the sheath may contain backward facing hooks 90 or the like to cause the sheath to be anchored to the surrounding tissue. As shown in FIGS. 2A–2D, a clip or similar mechanism can be used on the sheath to achieve hemostasis.

Figure 2A:
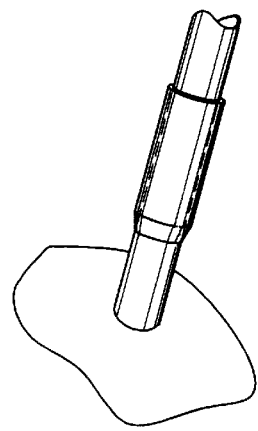
FIGS. 2A–2D are schematic illustrations of a post operative hemostasis procedure employing the sheath of FIG. 2.
Figure 2B:
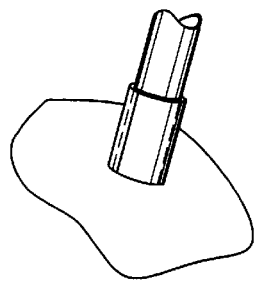
Figure 2C:
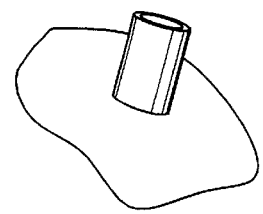
Figure 2D:
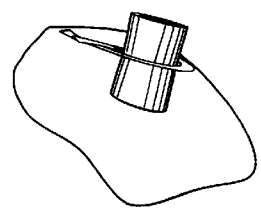

FIGS. 2A–2D are schematic illustrations of a post operative hemostasis procedure employing the sheath of FIG. 2. In FIG. 2A, a coring needle is shown at the end of a channel-forming procedure with the sheath disposed about the needle but not yet in contact with the tissue. FIG. 2B illustrates the insertion of the sheath into the channel. In FIG. 2C, the needle is removed and, in FIG. 2D, the sheath is clamped to seal the channel. It should be clear that other closures can be substituted for the clamp shown in FIG. 2D. For example the sheath may be self-clinching, or foldable or can be welded or fused by heat or chemical reaction. Alternatively, the sheath can be closed by the application of a Biocompatible glue. Both the sheath and the closure can be biodegradable over time, such that the closure will be replaced naturally as the tissue heals. In the preferred embodiment, as little of the sheath material is introduced into the channel as necessary for anchoring and sealing.

The volume of the tissue layer that is heated and denatured using the device is given by $$V = \pi d \delta l.$$

For a typical case, the thickness of the thermalized zone on the wall of the cored cylinder, $\delta$ will be about $\sqrt{\pi D \tau} = 0.01$ cm, the thermal diffusivity, D will be about $10^{-3}$ cm$^2$/sec, the diameter of the cored cylinder is d=0.1 cm, the electrical pulse width $\tau$ can be on the order of approximately 40 ms, and the length of the cored cylinder, l, is about 2 cm. Based on these parameters, V will be about $6 \times 10^{-3}$ cc.

The energy required for denaturation can be determined as follows.

$$E = V \rho_t C_v \Delta T,$$

where $C_v \approx 4$ J/gm is the heat capacity of tissue, $\rho_t$ is the density of the tissue, which is approximately 1 g/cc and $\Delta T$ is the temperature rise needed for denaturation. For a typical case with $\Delta T = 70°$ C. this results in an energy requirement of approximately 1.7 Joules. The device clearly uses substantially less energy in boring the channel than the approximately 40 Joules used in the conventional laser techniques. Consequently, the device in accordance with the present invention achieves the same results as that obtained with the more costly laser devices, but at a substantial reduction in the energy required to perform the process.

The energy dissipated in the resistive layer can be approximated by the formula $$E = I^2 R \tau$$

where $\tau$ is the pulse width of the current (I) required to generate and dissipate the desired energy into tissue. For typical values, $\delta$ is $\approx 0.1$ mm, $\tau \approx 40$ ms, $$I^2 R \approx 42.5 \text{ watts}$$

For illustrative purposes, with a current of 1 Ampere (I=1A), the ohmic resistance R will be approximately 43 $\Omega$. With a current of 0.1 Ampere (I=0.1A), the ohmic resistance R will be approximately 4.3 K$\Omega$. An embodiment with an ohmic resistance of 43 $\Omega$ is more desirable than an embodiment having a resistance of 4.3 K$\Omega$ since the required voltage from the supply at terminals TERM1 and TERM2 is lower. Less material is required to provide the necessary electrical isolation than if the higher voltage is used.

The electrically insulating layer 60 must be sufficiently thin such that it does not affect the thermal conduction rate to the contacting tissue. The choice of resistive material can be guided by the following equation:

$$R = \rho \frac{l}{\pi dt}$$

where $\rho$ is the resistivity of the resistive material, is the myocardial thickness approximately 2 cm, and t is the thickness of the resistive coating around a needle of diameter, d.

For R=43 $\Omega$, and a myocardial thickness, l, of about 2 cm, $$\rho/t = 6.8 \ \Omega$$

For nichrome with $\rho = 1.5 \times 10^{-4}$ $\Omega$cm, the resistance layer thickness is approximately $2.2 \times 10^{-5}$ cm (0.22 $\mu$m). While for graphite with $\rho = 1.4 \times 10^{-2}$ $\Omega$cm, the resistance layer thickness is about $2.1 \times 10^{-3}$ cm (21 $\mu$m). One of ordinary skill in the art will recognize that other material choices with commensurate adjustments in coating thickness will also be suitable for this application. A current of 2 Amperes correspondingly reduces the needed voltage to 21 volts, and the resistive thickness to 0.06 $\mu$m for nichrome and 5.3 $\mu$m for graphite. The application of these coated layers can be accomplished by standard coating techniques, which are well known in the art.

Referring to FIG. 1 and FIG. 2, in a preferred embodiment the coring needle 10 is a hollow cylindrical needle. The leading tip 70 is tapered and disposably attached to the needle 10. The body of the coring needle 10 is constructed in concentric layers. The outer layer is composed of a thermally conductive, electrically insulating material 60 which is inflexible, chemically neutral and thermally stable. Beneath the outer layer, are two coated layers: an electrically resistive portion 40 and a thin electrically conductive portion 50. The two layers 40, 50 are insulated electrically except at the leading edge 100 of the shaft 20, where they form an electrically conductive circuit. When joined together the two parts form a cylinder. When a current is introduced at the trailing end of the resistive portion 40, the current travels to the distal edge 100, uniformly deposits thermal energy into the resistive material, and returns via the thinner conductive portion 50. The inner lumen of the needle can also be coated with an electrically insulating and thermally insulating material.

Referring again to FIG. 2, the needle sheath 80 is fabricated in a generally cylindrical form and polished or lubricated for controlled insertion over the needle 10. The leading edge 110 of sheath 80 is beveled so as to lift the tissue to accommodate its slightly larger diameter. Adjacent to the trailing edge 120 are hooks 90 which are either bonded to the cylinder or raised from the cylinder's material by cutting and bending.

To perform a transmyocardial revascularization (TMR) procedure, the needle bore is inserted into the tissue. Accordingly, electrical energy is delivered to the resistive layer 40 generating sufficient thermal energy to heat the tissue in a known and controlled manner. The sheath 80 with hooks 90 can be inserted into the channel opening prior to needle 10 extraction, after heating. The sheath 80 is clipped off to achieve instant hemostasis.

For percutaneous coring, the needle head can be fitted to a catheter for introduction into the ventricle. The length of the needle can be restricted to avoid a puncture through the epicardium. No sheath is required for this approach, since the channel is started from the epicardium.

Figure 3:
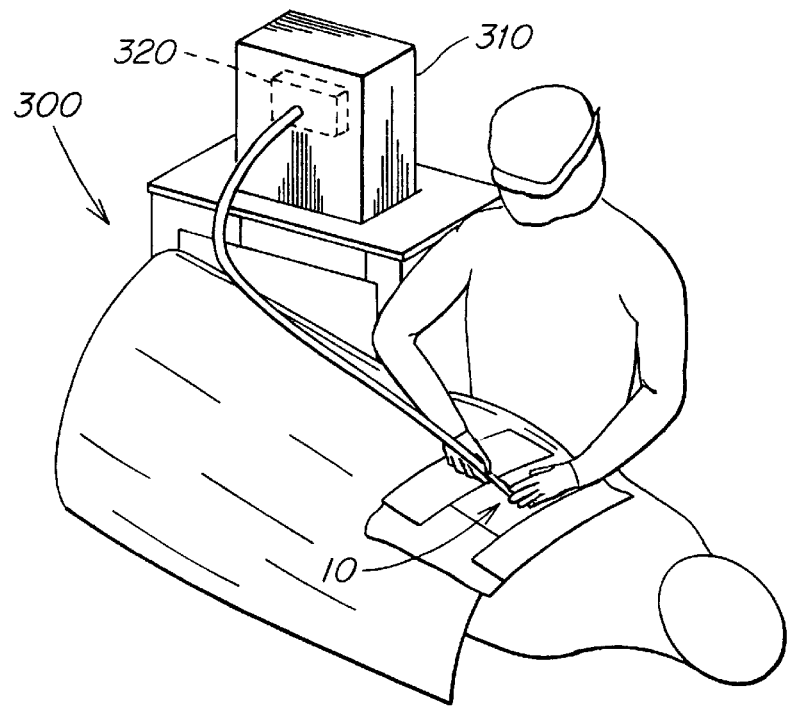
FIG. 3 is a schematic illustration of a patient undergoing transmyocardial revascularization according to the invention.

FIG. 3 illustrates a further embodiment 300 of the invention, in which a workstation console 310 connects to the needle 10 via a conventional electrical coaxial cable that provides power to the device. The workstation console 310 is portable, and sized to be placed on a cart or table for ease of use in the operating room. The console contains the switches, and meters sufficient for monitoring, delivering, and adjusting the transmission of bursts of electrical energy needed to core the channels in the myocardium. In this embodiment the console 310 delivers electrical energy in pulses between 5 and 50 milliseconds at selectable frequencies from the range of direct current to radio frequency. The means for generating electrical energy at different frequency ranges in selectable bursts is well known by those of ordinary skill in the art. A suction device 320 is included to clear the needle of tissue in between channel-forming operations so that the next channel can be readily cored.

Figure 4:
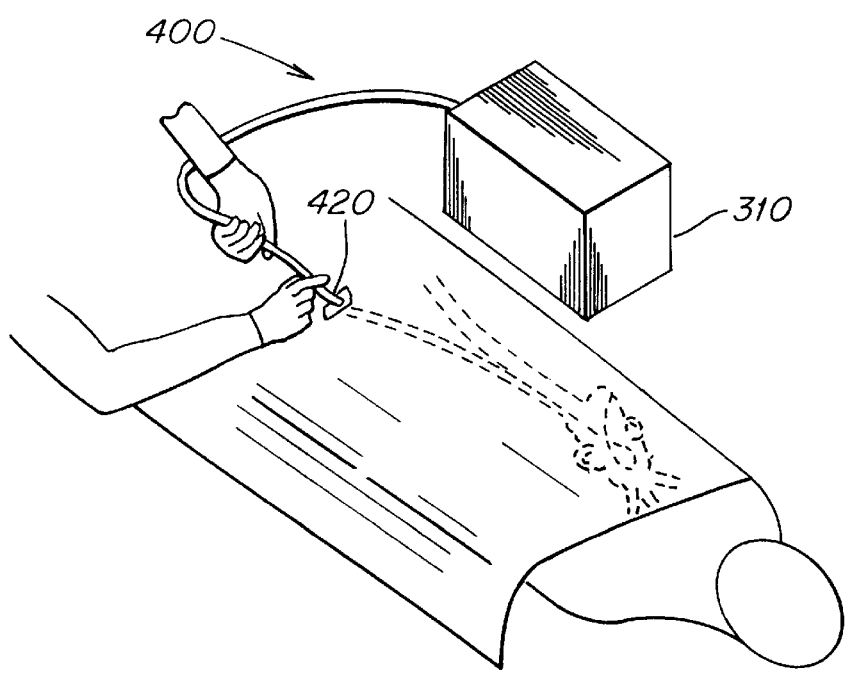
FIG. 4 is a schematic illustration of a patient undergoing percutaneous myocardial revascularization according to the invention.

In FIG. 4, a similar operating system 400 is shown for percutaneous TMR. In the illustrated use, the thermal needle of the present invention is incorporated into a catheter 420 and passed via the patient's blood vessels (e.g. via the femoral artery) into the inside of the heart. As passing over the aortic arch and into the ventricle, the needle 10 is deployed to form channels in the heart from within the ventricle or other portion of the heart muscle. The needle (and/or catheter) is again connected to a work station console 310, as described above, including suction means and various electronic controls.

Figure 5A:
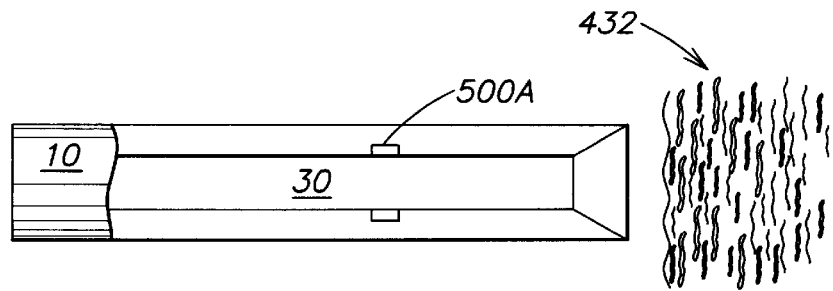
FIGS. 5A–5D are further schematic illustrations of a coring needle particularly useful in percutaneous applications.
Figure 5B:
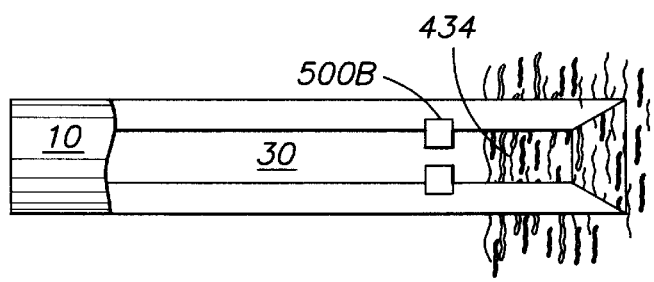
Figure 5C:
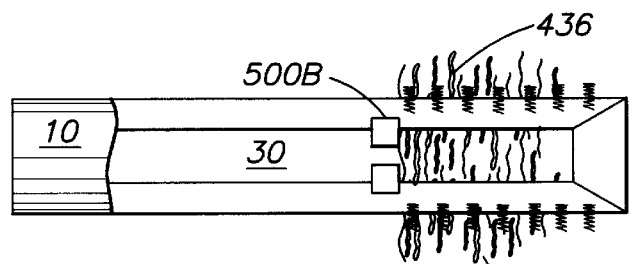
Figure 5D:
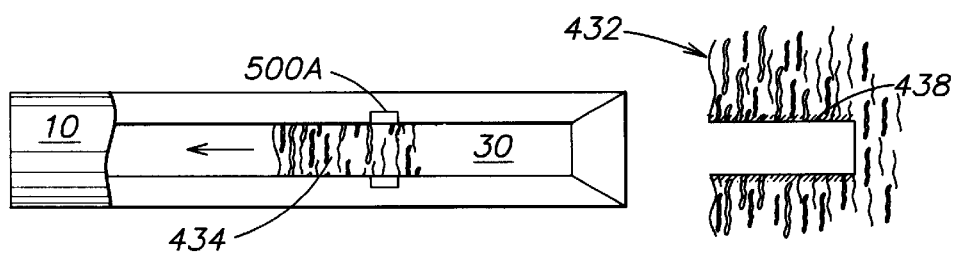

In FIGS. 5A–5D, an exemplary percutaneous operation is further illustrated. In FIG. 5A, the needle 10 is disposed adjacent to the target region of the heart wall 432. In this embodiment, the needle includes a heating mechanism (such as the resistive heating circuit described above in connection with FIG. 1) which is not shown for simplicity of illustration. Needle 10 has a hollow cavity 30 and a stopper mechanism which as shown is in a non deployed state 500A. As the needle is advanced to penetrate the heart wall, as shown in FIG. 5B, the stopper expands to limit the amount of heart tissue 434 which can be captured within the lumen 30 of the needle 10, thereby also limiting the needle's depth of penetration to ensure that the heart wall is not completely punctured. In FIG. 5C, the heating circuit of the needle is activated to provide thermal therapy to the surrounding myocardial region 436. FIG. 5D illustrates the removal of the cored tissue 434 via lumen 30 under suction and the removal of the needle for redeployment elsewhere in the heart. The treated region is left with a bore hole, the inner surface of which having undergone a transformation as the result of heating.

The processes illustrated in FIGS. 3 and 4 can be repeated numerous times to form a set of channels at predetermined locations or at sites appropriately chosen by the surgeon.

It is thus seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is as follows:

What is claimed is:

1. A surgical device for coring tissue comprising:
   a hollow shaft having a bore therethrough with an outer surface and an inner surface, and
   a sharpened distal end to bore through the tissue; and an electrical heating element, integrated in the shaft between the inner and outer surfaces, constructed and arranged to generate heat sufficient to at least partially denature the tissue adjacent to the outer surface of the shaft as the shaft passes through a channel in the tissue formed by said distal end of the device.

2. The surgical device of claim 1 wherein the device further comprises a suction source for applying a suction force to remove tissue from the hollow bore following deployment.

3. The surgical device of claim 1 wherein the heating element comprises a resistive circuit disposed within a body of the hollow shaft.

4. The surgical device of claim 3 wherein the resistive circuit further comprises a resistor selected from the group consisting of nichrome and carbon resistors.

5. The surgical device of claim 3 wherein the resistive circuit further comprises a layer of resistive material.

6. The surgical device of claim 5 wherein the layer of resistive material is at least partially cylindrical.

7. The surgical device of claim 5 wherein the resistive circuit further comprises an outer, at least partially cylindrical, resistive layer and a inner concentric conductive layer to facilitate current passage through the resistive material.

8. The surgical device of claim 3 wherein the resistive circuit comprises a helical winding of resistive material.

9. The surgical device of claim 3 further including an insulator for electrically isolating the resistive circuit from surrounding tissue.

10. The surgical device of claim 3 wherein the resistive circuit is connected to a voltage supply.

11. The surgical device of claim 1 wherein the shaft further comprises a polymeric material.

12. The surgical device of claim 1 wherein the shaft further comprises a polyimide material.

13. The surgical device of claim 1 further including a beveled tip coupled to said shaft for coring said tissue.

14. The surgical device of claim 13 wherein said tip is fabricated from stainless steel.

15. The surgical device of claim 1 wherein the said shaft is housed by a sheath, said sheath being slidably mounted about said shaft for introducing the sheath into the tissue and extracting said shaft therethrough.

16. The surgical device of claim 15 wherein one end of said sheath is beveled.

17. The surgical device of claim 15 wherein the sheath further comprises hooks to prevent extraction following introduction of the sheath over the shaft and into the tissue.

18. The surgical device of claim 15 wherein the sheath comprises a biodegradable material.

19. The surgical device of claim 15 wherein the sheath further comprises a closure.

20. A needle for coring a channel into the myocardium comprising:
   a hollow shaft including,
      a body having an inner surface defining a lumen and an outer surface in spaced apart relation to said inner surface, and a cutting edge at a distal end of said body sufficiently sharp to bore through a tissue; and an electrical heating element, disposed between the inner and outer body surfaces, for generating heat sufficient to at least partially denature tissue adjacent to said outer surface of the shaft body.

21. The needle of claim 20 wherein the device further comprises a suction source for applying a suction force to remove tissue from the hollow bore following deployment.

22. The needle of claim 20 wherein the heating element comprises a resistive circuit.

23. The needle of claim 22 wherein the resistive circuit further comprises a resistor selected from the group consisting of nichrome and carbon resistors.

24. The needle of claim 22 wherein the needle is adapted to treat a myocardium of a natural human heart.

25. The needle of claim 22 wherein said hollow shaft comprises electrically insulating thermally conductive material to electrically insulate the resistive circuit from the tissue while allowing heat generated by the resistive circuit to travel through the shaft to the tissue.

26. The needle of claim 20 wherein the said shaft is housed by a sheath, said sheath being slidably mounted about the shaft for introducing the sheath into the tissue and extracting the shaft therethrough.

* * * * *